United States Patent [19]

Adair

[11] Patent Number: 4,736,733

[45] Date of Patent: Apr. 12, 1988

[54] ENDOSCOPE WITH REMOVABLE EYEPIECE

[75] Inventor: Edwin L. Adair, Denver, Colo.

[73] Assignee: Medical Dynamics, Inc., Englewood, Colo.

[21] Appl. No.: 18,630

[22] Filed: Feb. 25, 1987

[51] Int. Cl.⁴ .............................................. A61B 1/06
[52] U.S. Cl. ....................................... 128/6; 604/264; 604/280; 604/283
[58] Field of Search .......................... 128/4, 5, 6, 7, 8; 604/264, 280, 283

[56] References Cited

U.S. PATENT DOCUMENTS

| | | | |
|---|---|---|---|
| 3,831,017 | 8/1974 | Auer | 128/6 X |
| 3,858,577 | 1/1975 | Bass et al. | 128/8 |
| 4,011,403 | 3/1977 | Epstein et al. | 358/209 |
| 4,254,762 | 3/1981 | Yoon | 128/4 |
| 4,269,192 | 5/1981 | Matsuo | 128/6 X |
| 4,313,431 | 2/1982 | Frank | 128/7 |
| 4,589,404 | 5/1986 | Barath et al. | 128/6 |
| 4,624,243 | 11/1986 | Lowery et al. | 128/6 |

Primary Examiner—William H. Grieb

Attorney, Agent, or Firm—Fields, Lewis, Pittenger & Rost

[57] ABSTRACT

A sterilizable catheter of micro-thin diameter has a central coherent fiber bundle for carrying an image to a viewing means, which is surrounded by light fibers. The proximate end of the catheter is provided with a coupling means for aligning the coherent optical bundle with the optical system of the viewing means and for providing an interface with light transmitting means to transmit light from a light source to the body cavity. The coupling means has a diameter no bigger than the diameter of the covering of the catheter. When the catheter is used in a trochar, the trochar can be removed while the catheter remains in place. This is accomplished by removing the viewing means and sliding the trochar over the catheter and then replacing the viewing means for further viewing within the body cavity. The catheter of this invention may be provided in various sizes, each having coupling means for reception in any one of a plurality of sockets in a video monitor which are sized for the various catheters to provide an image to the video monitor screen.

7 Claims, 2 Drawing Sheets

ENDOSCOPE WITH REMOVABLE EYEPIECE

TECHNICAL FIELD

This invention relates to a micro-thin endoscope and more particularly to such an endoscope having a coupling means on the proximate end for releasable attachment either to an eyepiece for direct viewing by the surgeon or to a console for viewing on a video screen or monitor.

BACKGROUND ART

Prior to this invention, light beams have been used both for illumination and for treatment of disease in patients. However, most of these instruments have not been of sufficiently small size that they can be passed through the various canals and openings of the body without discomfort to the patient. In some cases surgical procedures are required for introducing the instrument to the desired location within a body cavity.

U.S. Pat. No. 3,858,577 to Bass, et al. discloses an endoscope of substantial size for performing laser surgery. In this device, a conventional light is used through fiber optics to illuminate the operating site and laser light is used to perform a surgical procedure.

U.S. Pat. No. 4,011,403 to Epstein, et al. discloses a fiber optic laser endoscope. The device utilizes a laser beam as a light source and an optical fiber as a light transmitter. The sensing means includes a TV camera located at the investigated site. The laser beam produces three different wavelengths which produce white light. Also ultraviolet or infrared light can be used. The camera is separate from the fiber optics and the laser.

U.S. Pat. No. 4,313,431 to Frank discloses an endoscope deploying a laser light source with a light conducting fiber. This device is used for irradiating bladder tumors utilizing the laser light beam.

Many of the problems identified above have been overcome by the invention set forth in commonly assigned U.S. Pat. No. 4,589,404 to Barath, et al. wherein an endoscope, having a micro-thin diameter, is provided having an interface connector at the proximate end thereof for removably plugging into a receptacle in a video monitor. Thus, the endoscope can be separately sterilized and can be easily replaced, should it become damaged. However, if a power interruption should occur or a malfunction cause the monitor not to work properly, the catheter disclosed in that patent can no longer be used to complete the operation. This neccesitates removal and replacement of the catheter with another one having an integral eyepiece for viewing the body cavity. This requires extra time and inconvenience and is not desirable from the standpoint of the surgeon or the patient.

DISCLOSURE OF THE INVENTION

This invention relates to a sterilizable catheter for viewing and providing treatment within body cavities by nonsurgical or micro-surgical procedures. The catheter includes a coherent fiber optical bundle whose diameter is micro-thin which extends from a distal end to a point adjacent to the proximate end and has a planar surface at the distal end. In addition, a tubular inner cover extends over the bundle and a plurality of light transmitting fibers are spaced around the outer surface of the inner cover. A tubular outer cover extends over the fibers to hold them in place and the outer cover extends from the distal end to a point spaced from the proximate end. Optical lens means is provided at the distal end of the optical bundle to focus an image of a portion of the cavity on the distal end of the optical bundle for transmission through the optical bundle. A coupling means is also provided for removably connecting the catheter to a viewing means in fixed angular relationship. This coupling means is attached to the proximate end of the catheter and has a diameter no larger than the diameter of the outer cover so that the catheter can pass completely through a trochar lumen.

More particularly, the catheter has alignment means to angularly align the optical bundle with the viewing means in the form of a longitudinal groove extending along the coupling means for alignment with a longitudinal rib in the viewing means. The viewing means can include a removable eyepiece having a socket for slidably receiving the coupling means in aligned relationship for viewing and alternatively can include a console containing optics and a viewing screen having a socket for slidably receiving the coupling means when not on the eyepiece, for viewing the body cavity on the viewing screen. Conveniently, the console can also include a rotatable member having a plurality of sockets spaced therearound, each socket being of different diameter for accommodating catheters constructed in accordance with this invention which also have different diameters, wherein the rotatable member is selectively alignable with the optics of the console.

From the foregoing it can be seen that a novel method of using a sterilized catheter for viewing and/or treatment within body cavities is provided which includes inserting the distal end of the catheter into a body cavity, attaching a first removable optic means to the coupling means to view the body cavity, disconnecting the first removable optic means from the coupling means, and attaching a second removable optic means to the coupling means to view the body cavity.

In addition, since the optical means is removable, the catheter can be inserted through the lumen of a trochar which has been introduced into a body cavity, the optic means being attached to the coupling means for viewing. After viewing, the optic means can be disconnected and the trochar can be removed over the coupling means of the catheter and the optic means reattached for further viewing, as required.

Additional advantages of this invention will become apparent, when taken in conjunction with the accompanying drawings.

BEST MODE FOR CARRYING OUT THE INVENTION

Figure 1A:
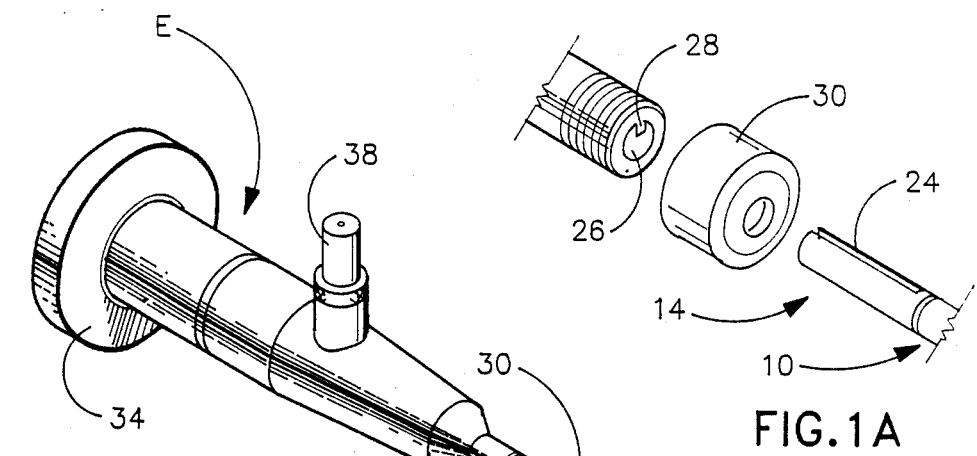
FIG. 1 is a perspective view of a catheter and eyepiece constructed in accordance with this invention showing specific details of the coupling means and the eyepiece.
Figure 1:
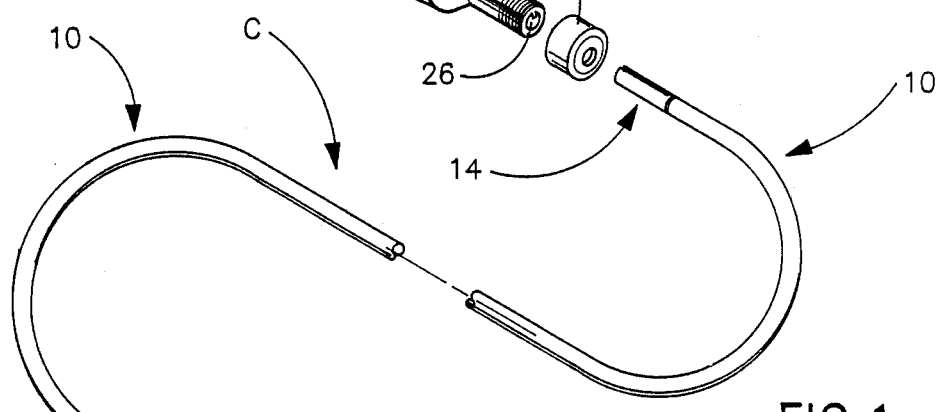
Figure 5:
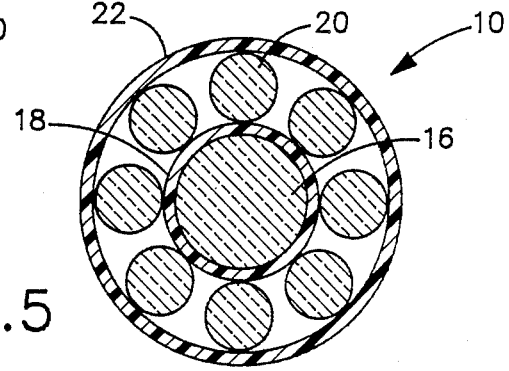
FIG. 5 is a cross section of a catheter constructed in accordance with this invention.

In accordance with this invention, a sterilizable micro-thin catheter C is provided as shown in FIG. 1. This catheter includes a cable assembly 10 which is provided at its distal end with a lens 12 and at its proximate end with a coupling means 14. Turning to FIG. 5, an enlarged cross section of cable assembly 10 is shown. At the center of the cable is a coherent fiber optical bundle 16, a tubular inner cover 18 extends around coherent optical bundle 16 and may be formed of a heat shrinkable Teflon material which extends along the coherent optical bundle from the distal end to the proximate end. Placed around inner covering 18 are a plurality of light carrying bundles 20 which are made up of individual fibers which do not have to be coherent. These bundles are for transmitting light from a suitable light source to the body cavity. An outer cover 22 extends around the spaced light bundles 20, as shown and may also be constructed of a heat shrinkable Teflon material which extends from the distal end of catheter 10 to a position adjacent coupling means 14.

Figure 2:
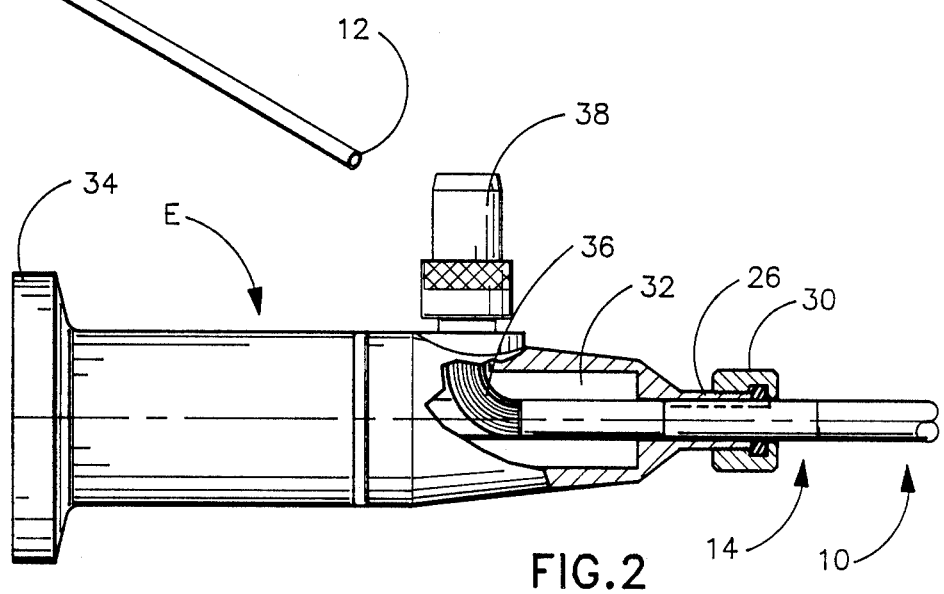
FIG. 2 is a fragmentary side elevation of the eyepiece of FIG. 1 showing the interconnection of the catheter and the optics within the eyepiece.

The coupling means 14 is located at the proximate end of outer cover 22 and includes a longitudinal groove 24 for alignment with a mating rib in a viewing means. It can be made of any suitable material, such as anodized aluminum or a machinable grade of plastic, such as Bakelite. One viewing means, constructed in accordance with this invention is eyepiece E shown in FIG. 1. It has a socket 26 with a longitudinal rib 28 that is alignable with the groove 24 of coupling means 14. Thus, the coupling means can be slid into the socket as best seen in FIG. 2 and held in position by threaded locking nut 30. The proximate end of coupling means 14 and the fibers are flat and polished so as to come into contiguous face-to-face contact with the optical system 32, which includes suitable lens for transmitting the light from the coherent fiber bundle to the user's eye which is held against the ocular face 34. The alignment of groove 24 with rib 28 assures that the image being transmitted by the coherent optical bundle 16 is in proper orientation with respect to the optical system 32 of eyepiece E. The optical system 32 also includes light fibers 36 which extend to a fixture 38 to which a suitable light source can be attached for illuminating the body cavity by transmitting light along fibers 36 and light bundles 20.

Figure 3:
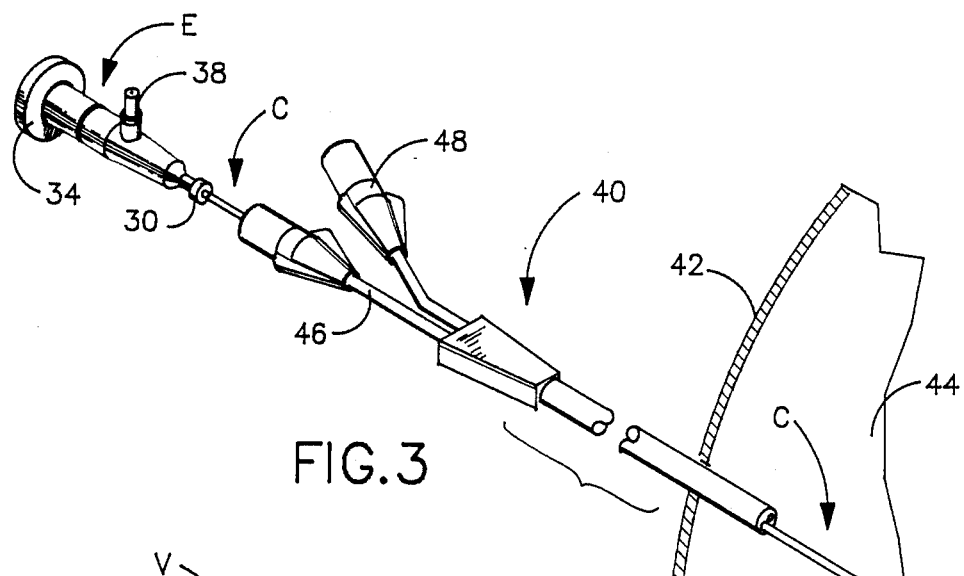
FIG. 3 is a perspective view showing the use of the catheter of this invention with a trochar which is inserted into a body cavity.

Because coupling means 14 has a diameter no larger than that of outer cover 22, it can be used in a more versatile manner than heretofore possible. FIG. 3 discloses a trochar 40 which is illustrated as being inserted through the wall 42 of a body member and into a body cavity 44. The trochar has a first lumen 46 through which the catheter C extends into the body cavity 44. A second lumen 48 is provided for any one of a number of purposes, such as for irrigation or treatment within the body cavity 44. As is well known, trochars of this type may have more than two lumens, depending on their intended use.

After the procedure is completed through lumen 48, it may be desirable to remove trochar 40 while leaving catheter C in place for further viewing. With the present invention this is possible. The eyepiece E is removed by removing locking nut 30 and sliding the coupling means 14 of the catheter out of socket 26. Since the coupling means 14 is no bigger in diameter than outer cover 22, the trochar can be slid to the left, as viewed in FIG. 3, while leaving catheter C in place. After removal of trochar 40, the eyepiece E can be reconnected to the coupling means 14, as previously described. The surgeon can then resume his viewing of the body cavity, as required.

Figure 4:
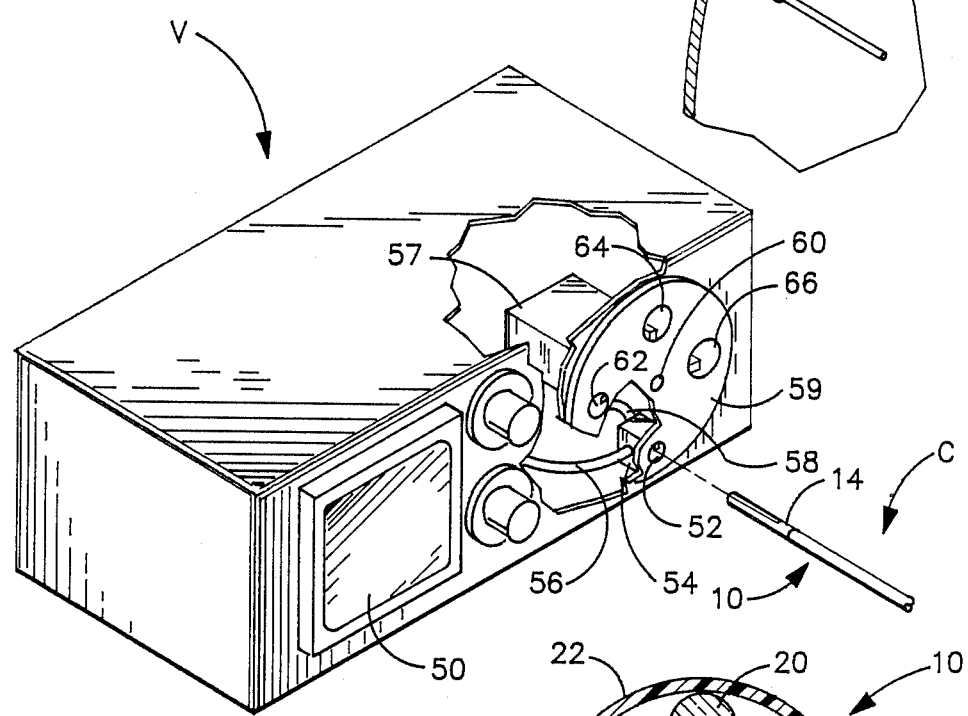
FIG. 4 is a perspective view of a console for use with the catheter of this invention.

Conveniently, the sterilizable catheter of this invention can also be used with a video console V, of the type shown in FIG. 4. This console includes a video screen 50. The coupling means 14 of catheter C is receivable in a socket 52 which is connected to the video screen 50 by suitable optics 54 which includes a coherent fiber bundle 56 for transmitting the image to video screen 50. A light source 57 is provided and is connected to the operative socket by light cable 58. It is contemplated that the invention might be utilized with catheters of different diameters for different purposes. Thus, socket 52 can be provided in a disc 59 which is mounted for rotation on the video console V about an axis 60 and is provided with a plurality of other sockets, such as sockets 62, 64 and 66, as shown. The socket corresponding to the size of the catheter can be rotated to be in the position of socket 52, so as to be properly aligned with the optics 54.

An important advantage of this invention is that when a cable assembly 10 of the catheter becomes damaged and no longer usable, it can replaced with another one without having to replace a corresponding eyepiece. Furthermore, the catheter of this invention can be made to be moisture impervious so that it can be easily sterilized for reuse. When used with a console, the sterility of the operating environment can be maintained since the surgeon does not need to put an eyepiece against his face. Furthermore, when the device is used with the video monitor V, should there be a power interruption or should the video monitor malfunction, it is merely necessary to slip the coupling means 14 of the catheter out of its socket, such as socket 52, and attach a sterilized eyepiece E, which would be provided to the surgeon, so that he can continue with the operation or procedure with minimal interruption.

From the foregoing, the advantages of this invention are readily apparent. A catheter has been provided which has great versatility in that it may be used with either a substantially standard eyepiece or with a video monitor. The catheters can be provided in different sizes when used with a video monitor, which may contain a plurality of sockets for alignment with the optical means of the video monitor for connection with a catheter of the selected size. Furthermore, the catheter can be used within the lumen of a trochar and since the eyepiece is removable the trochar can be removed without removing the catheter and then the eyepiece can be replaced for further viewing. Finally, the catheter can easily be replaced should it become damaged without replacement of the eyepiece which contains expensive lenses.

This invention has been described in detail with reference to particular embodiments thereof, but it will be understood that various other modifications can be effected within the spirit and scope of this invention.

I claim:

1. A sterilizable catheter for viewing and/or treatment within body cavities by nonsurgical or micro-surgical procedures and having a distal end for insertion into a body cavity and a proximate end, said apparatus comprising:

a coherent fiber optical bundle having a micro-thin diameter and extending from said distal end to a point adjacent said proximate end and having a planar surface at its proximate end;

a tubular inner cover extending over at least a portion of said bundle;

a plurality of light transmitting fibers spaced around said inner cover;

a tubular outer cover extending over said fibers to hold them in place, said outer cover extending from said distal end to a point spaced from said proximate end;

optical lens means at said distal end of said optical bundle to focus an image of a portion of the cavity on said distal end of said optical bundle for transmission through said optical bundle; and a coupling means for removably connecting said catheter to a viewing means in fixed angular relationship, fixedly attached to said proximate end of said catheter and having a diameter no larger than the diameter of said outer covering so that said catheter can pass completely through a trochar lumen.

2. A catheter, as claimed in claim 1, wherein said coupling means includes:

alignment means to angularly align the optical bundle with said viewing means.

3. A catheter, as claimed in claim 2, wherein said alignment means includes:

a longitudinal groove extending along said coupling means for alignment with a longitudinal rib in the viewing means.

4. A catheter, as claimed in claim 2, wherein said viewing means includes:

a removable eyepiece having a socket for slidably receiving said coupling means in aligned relationship for viewing; and a console containing optics and a viewing screen having a socket for slidably receiving said coupling means when not on said eyepiece, for viewing the body cavity on said viewing screen.

5. A catheter, as claimed in claim 4, wherein said console includes:

a rotatable member having a plurality of sockets spaced therearound selectively alignable with said optics, each socket being of a different diameter for accommodating catheters of different diameters.

6. A method of using a sterilizable catheter for viewing and/or treatment within body cavities by nonsurgical or micro-surgical procedures which has a distal end for insertion into a body cavity and a proximate end with coupling means of no greater diameter than the body of the catheter, said method comprising the steps of:

inserting the distal end of the catheter into a body cavity;

attaching a first removable optic means to the coupling means to view the body cavity;

disconnecting the first removable optic means from the coupling means; and attaching a second removable optic means to the coupling means to view the body cavity.

7. A method of using a sterilizable catheter for viewing and/or treatment within body cavities by nonsurgical or micro-surgical procedures which has a distal end for insertion into a cavity and a proximate end with coupling means of no greater diameter than the body of the catheter, said method comprising the steps of:

inserting a trochar into a body cavity;

inserting the catheter into the body cavity through the lumen of the trochar;

attaching a removable optic means to the coupling means;

viewing the body cavity through the catheter via the optic means;

disconnecting the optic means from the coupling means;

removing the trochar over the coupling means of the catheter while leaving the catheter in place;

reattaching the optic means to the coupling means; and resuming the viewing of the body cavity through the catheter via the optic means.

* * * * *